United States Patent
Min et al.

(10) Patent No.: US 11,911,553 B2
(45) Date of Patent: Feb. 27, 2024

(54) SYSTEMS AND METHODS FOR CONCENTRATING CELLS WITH A SYRINGE AND A CENTRIFUGE

(71) Applicant: Fenwal, Inc., Lake Zurich, IL (US)

(72) Inventors: Kyungyoon Min, Kildeer, IL (US); Christopher J. Wegener, Libertyville, IL (US); Alexander Dodge, Lincolnshire, IL (US)

(73) Assignee: Fenwal, Inc., Lake Zurich, IL (US)

( * ) Notice: Subject to any disclaimer, the term of this patent is extended or adjusted under 35 U.S.C. 154(b) by 1290 days.

(21) Appl. No.: 16/442,671

(22) Filed: Jun. 17, 2019

(65) Prior Publication Data

US 2020/0009312 A1 Jan. 9, 2020

Related U.S. Application Data

(60) Provisional application No. 62/694,601, filed on Jul. 6, 2018.

(51) Int. Cl.
*A61M 1/36* (2006.01)
*A61M 1/02* (2006.01)
*B01L 3/00* (2006.01)

(52) U.S. Cl.
CPC ........ *A61M 1/3692* (2014.02); *A61M 1/0272* (2013.01); *A61M 1/0281* (2013.01); *A61M 1/3693* (2013.01); *A61M 1/362227* (2022.05); *A61M 1/362265* (2022.05); *B01L 3/502* (2013.01); *A61M 1/36224* (2022.05); *B01L 2400/0409* (2013.01)

(58) Field of Classification Search
CPC ... A61M 1/36; A61M 1/02; B01L 3/50; B01L 3/00; B04B 5/04; B04B 5/0407; B04B 5/0414; B04B 2005/0435
See application file for complete search history.

(56) References Cited

U.S. PATENT DOCUMENTS 4,509,941 A * 4/1985 Johnson ................ B04B 5/0407
494/45
6,733,433 B1 * 5/2004 Fell ...................... A61M 1/3698
494/56

(Continued)

FOREIGN PATENT DOCUMENTS

JP 6469287 B1 * 2/2019
WO WO-2004088283 A2 * 10/2004 ........... A01N 1/0284

OTHER PUBLICATIONS

European Patent Office, Extended European Search Report, counterpart EP Appl. No 19182291, dated Nov. 5, 2019 (8 pages).

*Primary Examiner* — Walter D. Griffin
*Assistant Examiner* — Cameron J Allen
(74) *Attorney, Agent, or Firm* — Cook Alex Ltd.

(57) ABSTRACT

A system for concentrating cells, wherein a syringe comprises a lumen and an axial end comprising a port and a radial end closed to liquid flow. A plunger divides the axial and radial ends, and the syringe is configured to hold a cellular suspension. A filter disposed at the radial end is configured to maintain sterility of the syringe. A cap comprises a vent disposed at the radial end. The plunger is configured to be actuated towards the axial end by air pressure being applied into the radial end and the plunger is configured to be actuated towards the radial end by a vacuum being applied into the radial end.

17 Claims, 15 Drawing Sheets

(56) References Cited

U.S. PATENT DOCUMENTS

| | | | |
|---|---|---|---|
| 2006/0148678 A1* | 7/2006 | Bauer | A61P 35/00 514/19.3 |
| 2006/0205581 A1 | 9/2006 | Chammas | |
| 2009/0148678 A1* | 6/2009 | Hwang | H05K 1/0281 428/209 |
| 2013/0092630 A1 | 4/2013 | Wegener | |
| 2013/0341291 A1 | 12/2013 | Wegener et al. | |
| 2014/0142464 A1* | 5/2014 | Harms | A61B 10/0233 606/180 |
| 2014/0148325 A1 | 5/2014 | Jo et al. | |
| 2014/0199680 A1 | 7/2014 | Min et al. | |
| 2017/0204371 A1 | 7/2017 | Wegener | |
| 2018/0155070 A1* | 6/2018 | Min | B65B 3/26 |

* cited by examiner

SYSTEMS AND METHODS FOR CONCENTRATING CELLS WITH A SYRINGE AND A CENTRIFUGE

FIELD OF THE DISCLOSURE

The present disclosure relates generally to systems and methods of washing biological cell suspensions and, in particular to systems and methods for washing and/or concentrating small volumes of cells with a syringe and a centrifuge.

BACKGROUND

Many therapies and laboratory protocols currently include practices in which a targeted cellular component (e.g., red blood cells, white blood cells, platelets) is separated from a cell suspension, e.g., whole blood, and stored for later use, e.g., infusion to a patient. The targeted cellular component may be in a suspension that includes a supernatant, e.g., plasma. It may be desirable to wash the cell suspension with a wash solution, e.g., saline, to remove the supernatant as well as any nontarget cellular material prior to later use.

Large volumes of wash solution are often used to clear processed fluid through fluid systems used to concentrate the target cells into final volumes ranging from approximately 50 ml to 5,000 ml. There may, however, be instances in which smaller final volumes (e.g., 10 ml or less) are desired, such as when processing single-dose quantities of blood cell products.

SUMMARY

According to an exemplary embodiment, the present disclosure is directed to a system for concentrating cells. A syringe comprises a lumen and an axial end comprising a port and a radial end closed to liquid flow. A plunger divides the axial and radial ends, and the syringe is configured to hold a cellular suspension. A filter disposed at the radial end is configured to maintain sterility of the syringe. A cap comprises a vent disposed at the radial end. The plunger is configured to be actuated towards the axial end by air pressure being applied into the radial end and the plunger is configured to be actuated towards the radial end by a vacuum being applied into the radial end.

According to an exemplary embodiment, the present disclosure is directed to a method concentrating a cell suspension with a centrifuge. Provided is a syringe comprising an axial end comprising a port and a radial end closed to liquid flow. A plunger divides the axial and radial ends, and the syringe is configured to hold a cellular suspension. Provided is a syringe holder configured to fit in a cavity of a centrifuge rotor having an axis of rotation. The syringe holder is configured to receive the syringe containing the cellular suspension with the axial end disposed towards an axial direction relative to the axis of rotation and the radial end disposed towards a radial direction relative to the axis of rotation. A first volume of the cell suspension is drawn into the axial end of the syringe. The syringe containing the first volume is centrifuged within the syringe holder with the port of the axial end disposed closer to the axis of rotation relative to the radial end of the syringe. Centrifuging is performed until the first volume is separated into pelletized cells and a supernatant. The supernatant is expressed off from the syringe until the axial end of the syringe comprises the pelletized cells and a desired volume of supernatant. The pelletized cells are resuspended in the desired volume of supernatant to arrive at a final cell product.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Some embodiments may allow for washing and concentration operations to be performed either manually or automatically.

Some embodiments may allow for syringes used for concentration of cells to be compatible with commercially available centrifuges.

Some embodiments may allow for ease of integration into a cell processing platform capable of upstream and downstream manipulations before and after target component separation.

Some embodiments may allow for a greater than 98% recovery of cells from initial cell suspension volumes of less than 50-60 mL.

During processing of cellular or blood components, cell concentration may be a required element of the workflow. This may be because upstream processing of cells did not concentrate cells to a desired degree and/or additional cell washing steps are desired. Cell concentration may take place as part of a larger automated process or may take place independently. Systems and methods for cell washing are exemplified by US Patent Publication Nos. 2013/0341291, 2013/0092630, 2014/0199680, and 2017/0204371, each of which is incorporated herein by reference. Cell washing methods may utilize systems and fluid circuits including a spinning membrane separator. Such systems may include peristaltic pumps and pinch valves that act on tubing to direct flow within the fluid circuit, although any suitable flow actuation system may be used.

Figure 1:
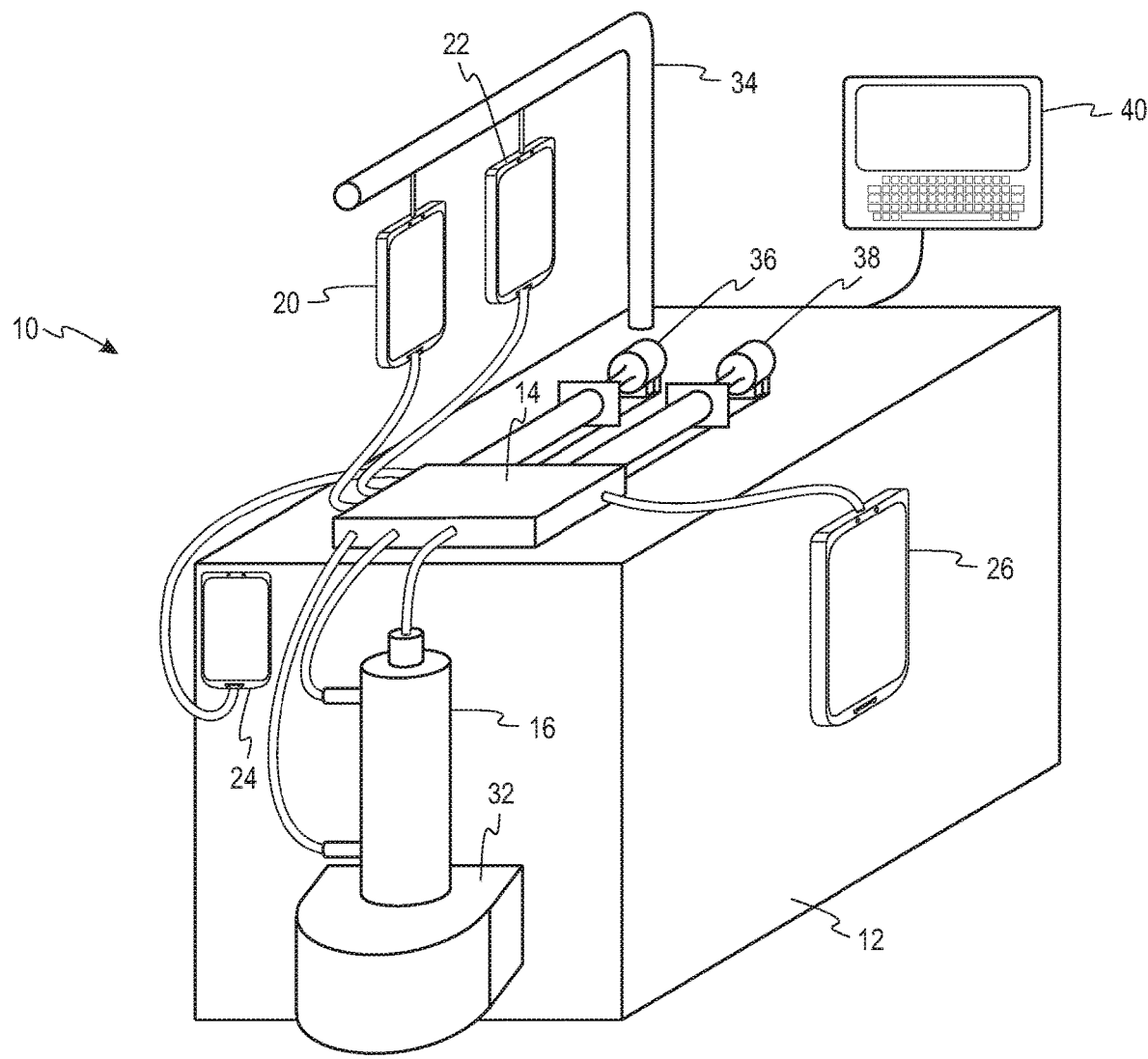
FIG. 1 is a perspective view of a system for washing small volumes of cellular suspensions, according to an exemplary embodiment.
Figure 2:
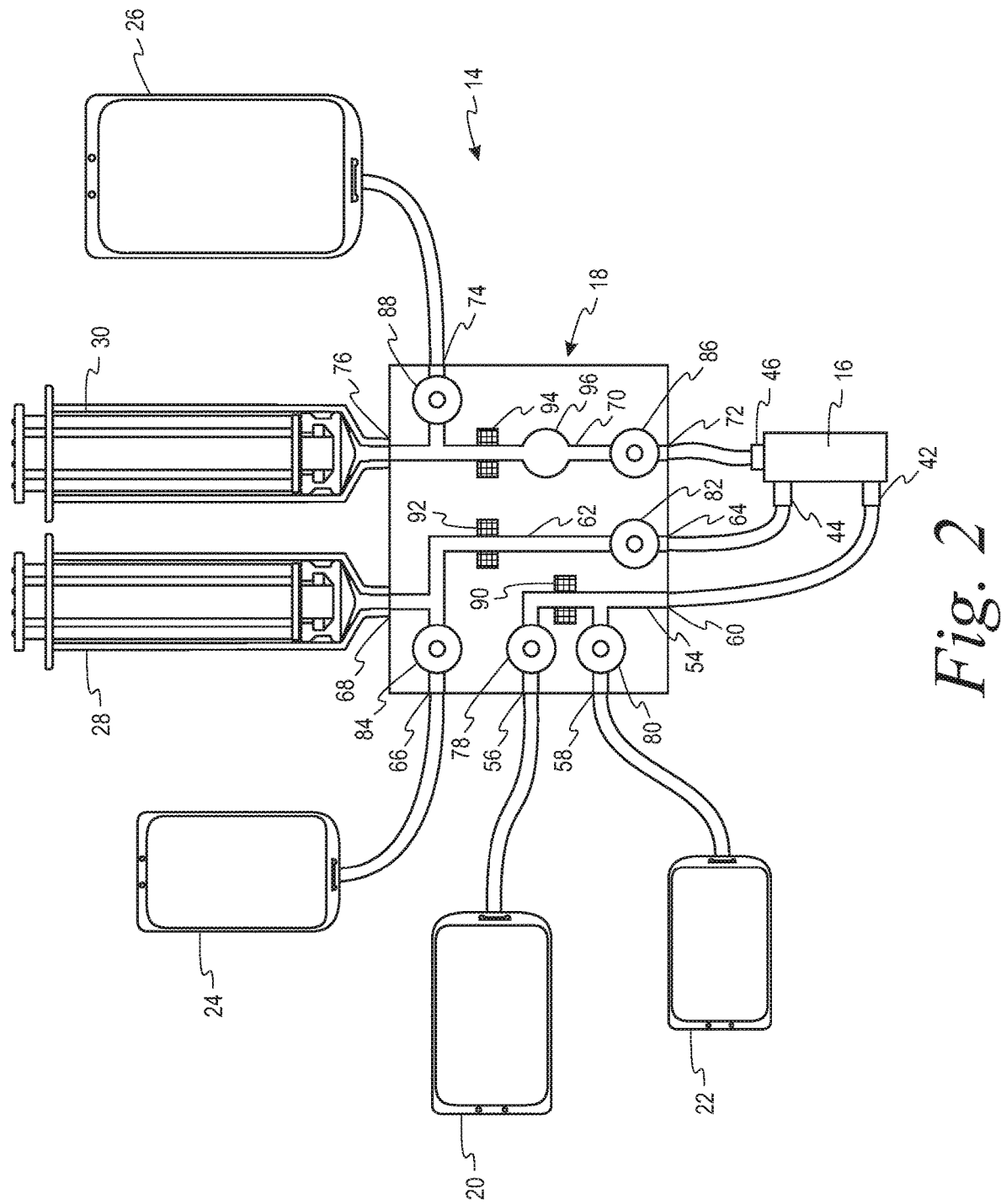
FIG. 2 is a schematic view of a disposable kit for use in the system of FIG. 1, according to an exemplary embodiment.

In an exemplary embodiment in which cell concentration takes place as part of a larger process, FIG. 1 shows a system 10 for cell washing including a reusable hardware component 12 and a disposable kit component 14, best seen in FIG. 2. The disposable kit 14 may include a spinning membrane separator 16, a cassette 18, for providing fluid management through the kit, and various containers 20, 22, 24 and 26, and one or more syringes 28, each comprising a body or barrel portion and a plunger. Tubings interconnect each of the various containers, as well as the inlet and outlets of the spinning membrane separator, to the cassette. Each syringe may be configured to be removably connected to the disposable kit 14. The reusable hardware component 12 may include a drive system/support 32 for the spinning membrane separator 16, supports 34 for the various containers of the disposable kit, a syringe pump 36, 38 for each syringe 28, and a programmable controller 40 for automatically controlling operation of the system.

The disposable kit 14 may comprise a spinning membrane separator 16 having an inlet 42 for flowing the suspension of cellular material to be washed and a wash medium into the spinning membrane separator, a first outlet 44 for flowing retentate comprising washed cells from the spinning membrane separator, and a second outlet 46 for flowing filtrate comprising supernatant of the cellular suspension and wash medium from the spinning membrane separator. The kit may further include containers 24, 26 for receiving the retentate and the filtrate, respectively, and either may include a container 22 of wash medium integrally connected to the kit at the time of manufacture or is configured to be connected to a container of wash medium at the point of use.

Fluid management of the kit 14 may be controlled by the controller 40 and the cassette 18. The cassette 18 may comprise a housing 52 having a series of fluid pathways therein interconnecting the various other components of the disposable kit, each of the fluid pathways having flow control mechanisms, such as valves/clamps and air detectors/pressure sensors associated therewith that are automatically operated by the controller 40. By having the valves/clamps, detectors and sensors integral with the cassette, the lengths of the tubings interconnecting the various containers of the system to the cassette may be minimized, thus reducing the internal volume of the kit.

Figure 3:
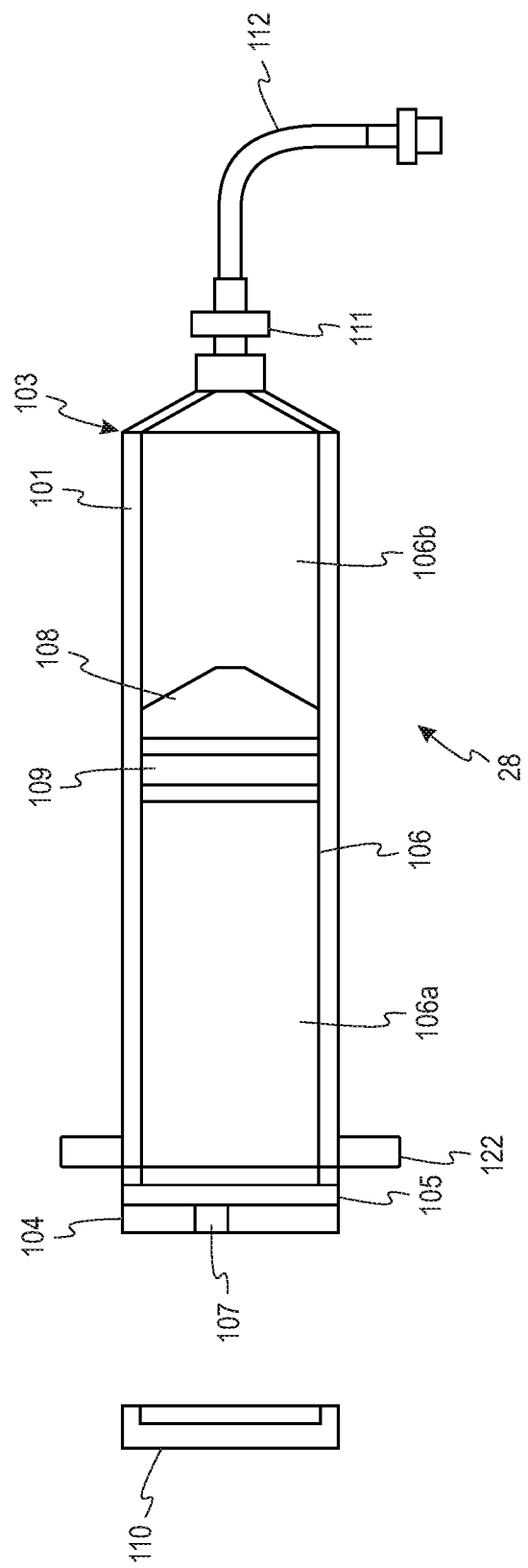
FIG. 3 is a diagrammatic illustration of a syringe, according to an exemplary embodiment.

Turning to FIG. 3, a diagrammatic illustration of the syringe 28 is shown, according to an exemplary embodiment. Syringe 28 may be used as part of a larger system such as system 10 of FIGS. 1-2. Syringe 28 may also be used independently and/or manually to collect and concentrate cells. The syringe may be disposable and configured for later centrifugation for yielding small volume cell products, e.g., pelletization. The syringe 28 may be suitable for liquid nitrogen storage. In one embodiment, the syringe 28 may be similar in shape, size, and material to a commercially available Schott 50 mL syringe, although any size, shape, and type of syringe suitable for the desired cell concentration and final volume may be used. The syringe 28 may comprise an elongated hollow barrel 101 that may be generally cylindrical in shape. The barrel 101 may comprise a radial end 102 configured for insertion into a centrifuge such that centrifugation results in higher density components collecting at the radial end according to known centrifugation principles. The other end of the barrel 101 may comprise an axial end 103 configured for insertion into a centrifuge such that centrifugation results in lower density components collecting at the axial end 103 relative to the radial end 102. Inside a centrifuge, the axial end 103 is configured to be disposed closer to the axis of rotation of the centrifuge than the radial end 102. Within the lumen 106 of the hollow barrel 101 may comprise a plunger 108 for actuating fluid flow within the syringe 28 and dividing the lumen 106 into a radial side lumen 106a and an axial side lumen 106b. The plunger 108 may comprise a visible indicator 109 (e.g., reflective stripe) allowing a user or sensor system to ascertain the location of the plunger 108 between the two ends 102 and 103 to determine volume of fluid within the syringe 28.

The radial end 102 of the barrel 101 of the syringe 28 may be capped by a vented cap 104 comprising a filter 105, which may provide a sterility barrier between the lumen 106 of the syringe 28 and the surrounding environment. In one embodiment, the filter may comprise pore sizes in the range of 0.2 to 0.45 microns. In one embodiment, the filter may be a commercially available 0.22 micron filter. The cap 104 may comprise an air vent 107 adjacent to the filter 105. The air vent 107 may be connected to a pneumatic pump able to apply a vacuum or air pressure to the radial side lumen 106a to control actuation of the plunger 108. A secondary cap 110 may be used to cover the radial end 102 when plunger actuation is not taking place and/or the syringe 28 is otherwise not in use.

The axial end 103 of the barrel 101 of the syringe 28 may terminate in a connecting port 111 through which fluid may enter or exit. The port 111 may be any suitable connecting port system, such as a luer connector, a needle, a cannula, a tubing, etc. In one embodiment, if the syringe 28 is used as part of a larger system such as the system 10 of FIGS. 1-2, the port 111 may be pre-connected with any of the components of the disposable kit 14. In another embodiment, the port 111 may be attachable to a sterile weldable tubing 112 that may be sterilely connected to another fluid container or system.

Figure 4A:
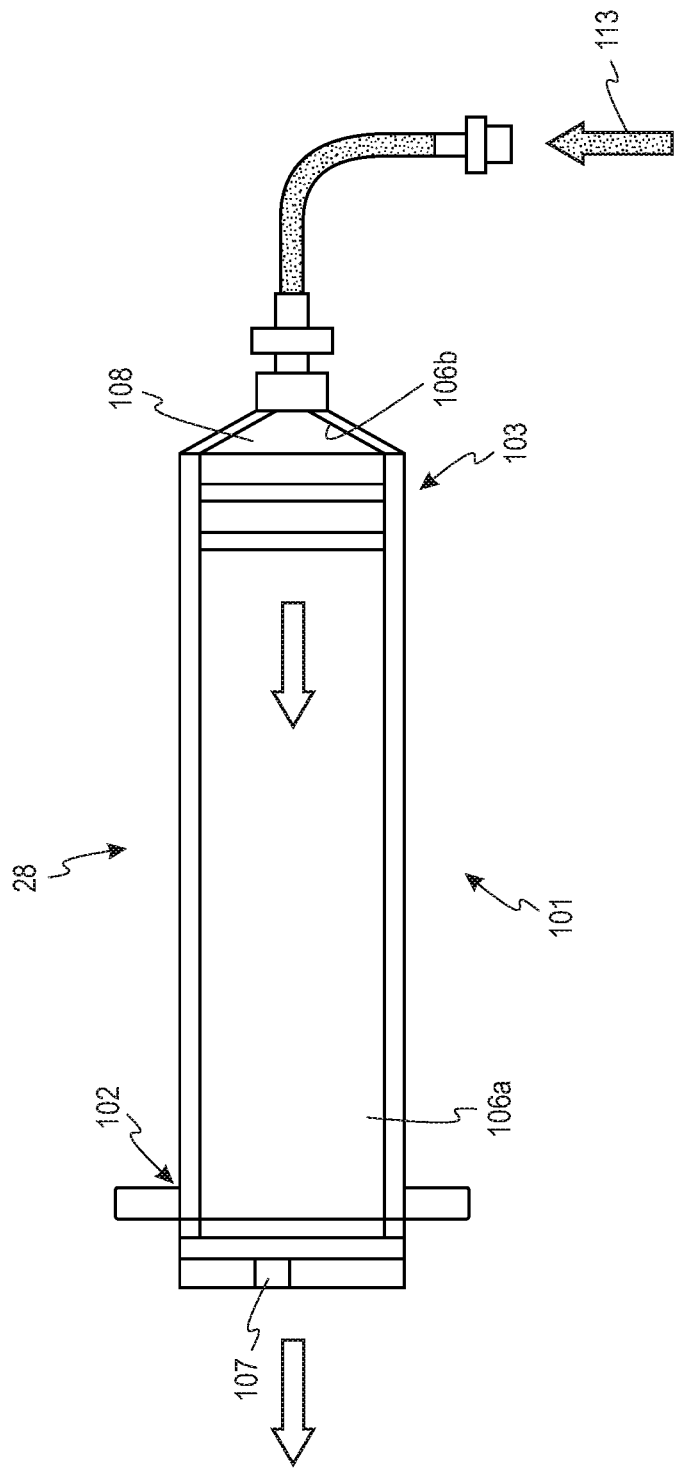
FIGS. 4A and 4B are diagrammatic illustrations of a pneumatic mechanism by which the syringe of FIG. 3 is filled with fluid, according to an exemplary embodiment.
Figure 4B:
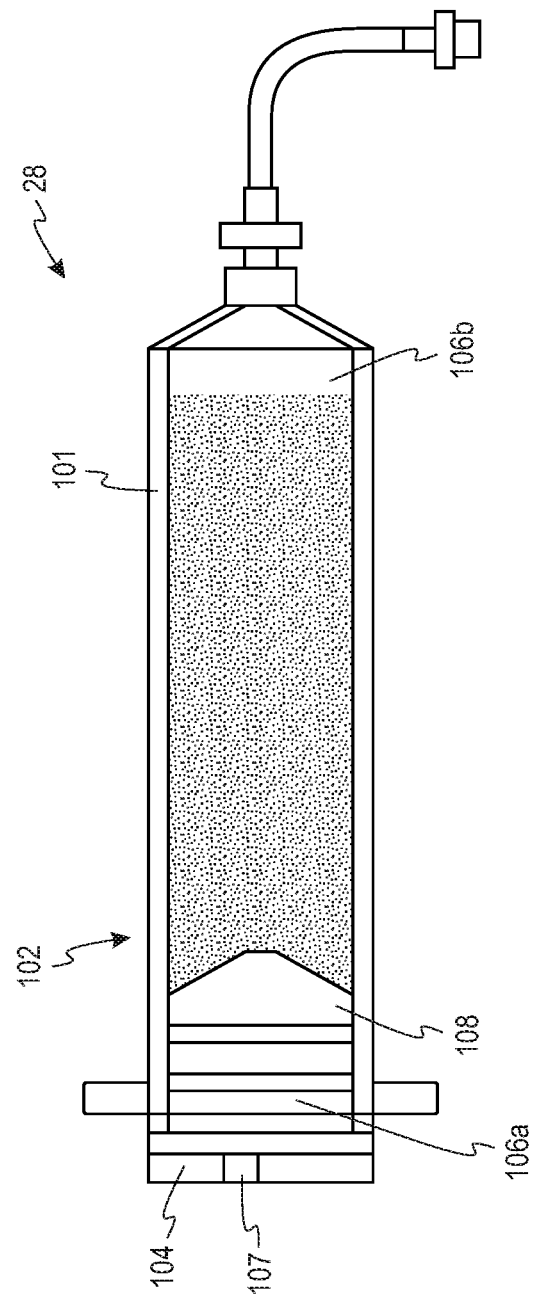

FIGS. 4A and 4B illustrate a pneumatic mechanism by which the syringe 28 may be filled with fluid, according to an exemplary embodiment. The port 111 of the syringe 28 may be connected to a cell suspension source 113 containing target cells to be processed. As shown in FIG. 4A, prior to commencing fluid fill, the plunger 108 may be pushed against the axial end of the barrel 101. To initiate fluid fill, a vacuum may be applied by a syringe pump 36, 38 (FIG. 1) to the radial side lumen 106a via the air vent 107, reducing pressure within the radial side lumen 106a. The decrease in pressure may actuate the plunger 108 towards the radial end 102, drawing the cell suspension into the axial side lumen 106b via the port 111.

The vacuum may be applied to the radial side lumen 106a of the syringe 28 until a desired volume of cell suspension has been drawn into the syringe 28. Once the desired volume has been drawn, the application of the vacuum to the radial side lumen 106a may continue until the plunger 108 is pulled against the radial end 102 of the barrel 101, as shown in FIG. 4B, while air is drawn into the axial side lumen 106b instead of the cell suspension. Once the plunger 108 has been pulled all the way against the radial end 102 of the barrel 101, the air vent 107 of the cap 104 may be released to equalize pressure between the lumen 106 of the syringe and the surrounding atmosphere.

Figure 5A:
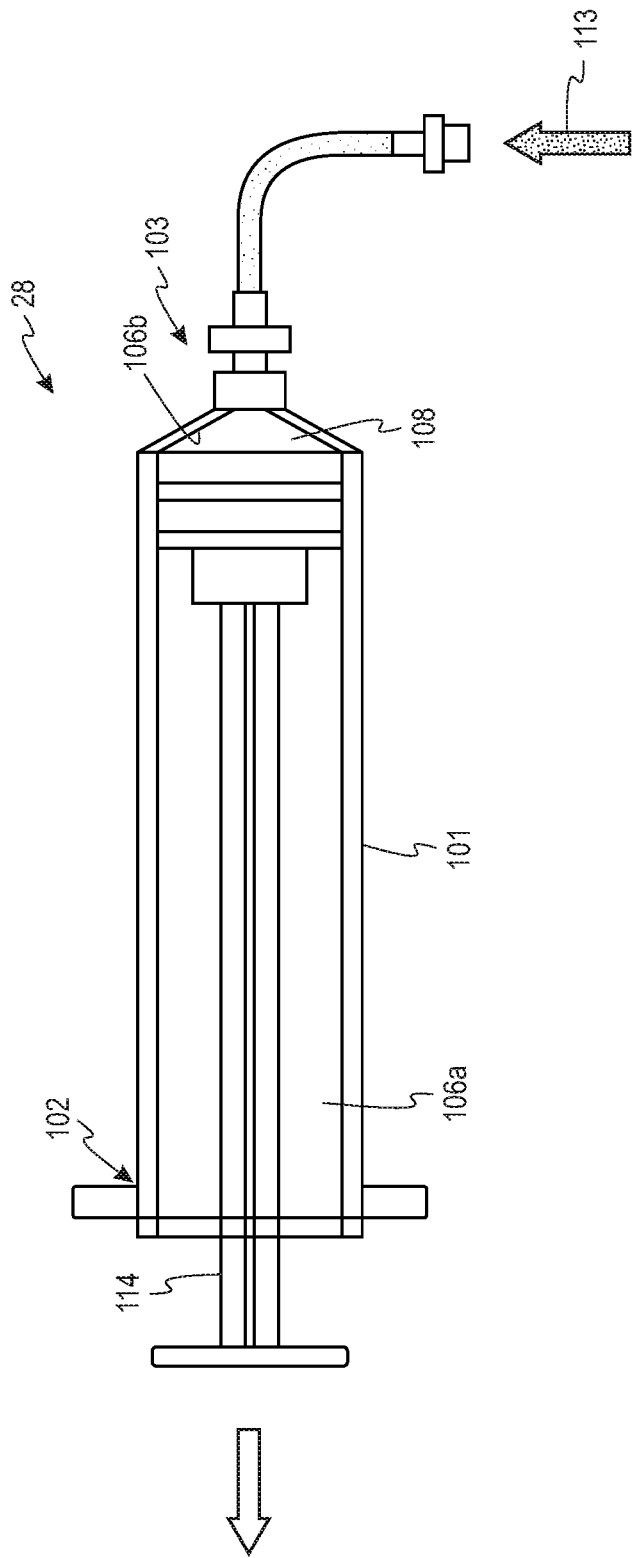
FIGS. 5A-5C are diagrammatic illustrations of a manual or a solid contact force mechanism by which the syringe of FIG. 3 is filled with fluid, according to an exemplary embodiment.
Figure 5B:
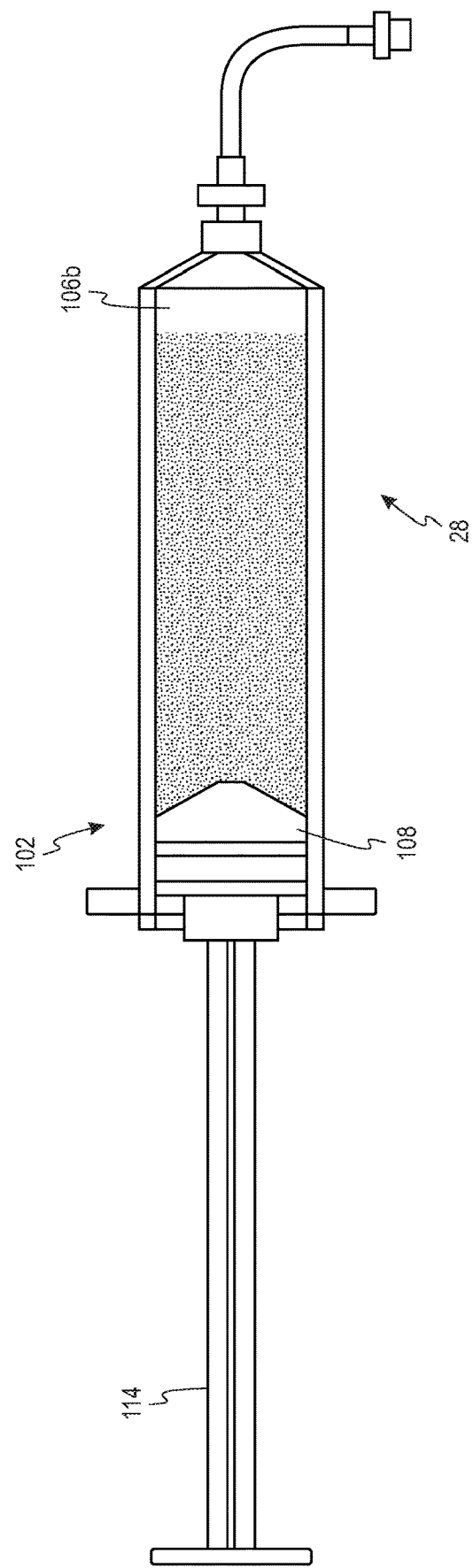
Figure 5C:
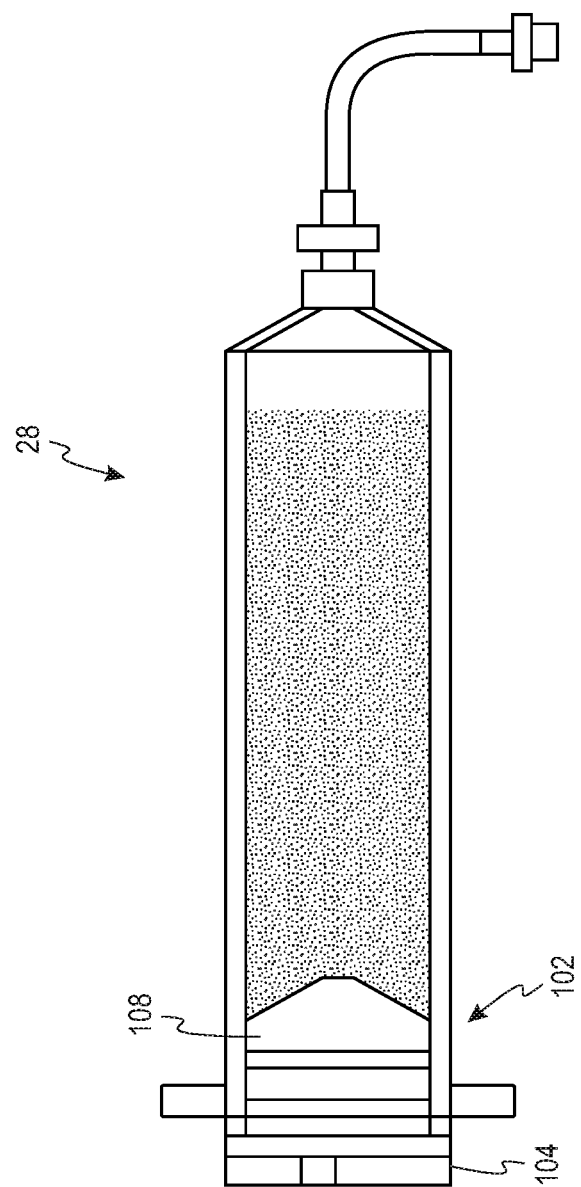

Alternatively, FIGS. 5A-5C illustrate a manual or a solid contact force mechanism by which the syringe 28 may be filled with fluid, according to an exemplary embodiment. As shown in FIG. 5A, in a sterile environment, the cap 104 of FIGS. 4A and 4B may be removed from the syringe 28 to expose the radial side lumen 106a of the barrel 101. A handle 114 configured for removable attachment with the plunger 108 may be inserted into the radial side lumen 106a and attached to the plunger 108. The handle 114 and the plunger 108 may be attached through any suitable means, e.g., interference fit, screw fit, etc. As shown in FIG. 5A, prior to commencing fluid fill, the plunger 108 may be pushed against the axial end 103 of the barrel 101. To initiate fluid fill, the handle 114 may be pulled manually or via a machine towards the radial end 102 to actuate the plunger 108 towards the radial end 102, drawing the cell suspension into the axial side lumen 106b via the port 111. The handle 114 may be pulled towards the radial end 102 until a desired volume of cell suspension has been drawn into the syringe 28. Once the desired volume has been drawn, the handle 114 may continue to be pulled until the plunger 108 is pulled against the radial end 102 of the barrel 101, as shown in FIG. 5B, while air is drawn into the axial side lumen 106b instead of the cell suspension. Once the plunger 108 has been pulled all the way against the radial end 102 of the barrel 101, the handle 114 may be removed from the plunger 108 and the cap 104 placed back onto the radial end 102 of the syringe 28, as shown in FIG. 5C.

Figure 6:
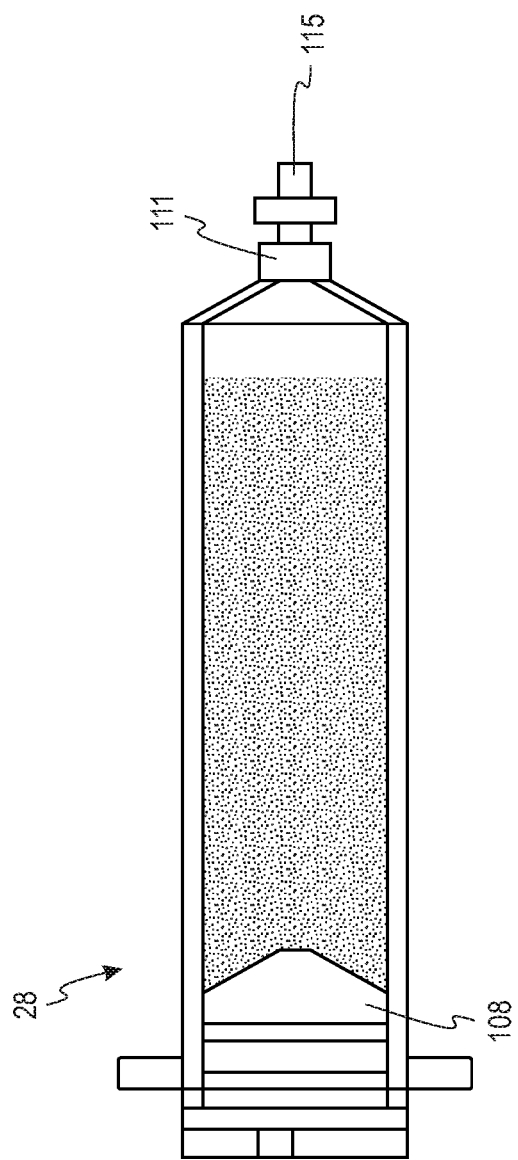
FIG. 6 is a diagrammatic view of a fluid-filled syringe ready for centrifugation, according to an exemplary embodiment.

Once the desired cell suspension volume has been drawn into the syringe 28, the port 111 may be disconnected from the cell suspension source 113 (FIGS. 4A and 5A) and be covered with a non-permeable tip 115, as shown in FIG. 6, in preparation for centrifugation.

Figure 7A:
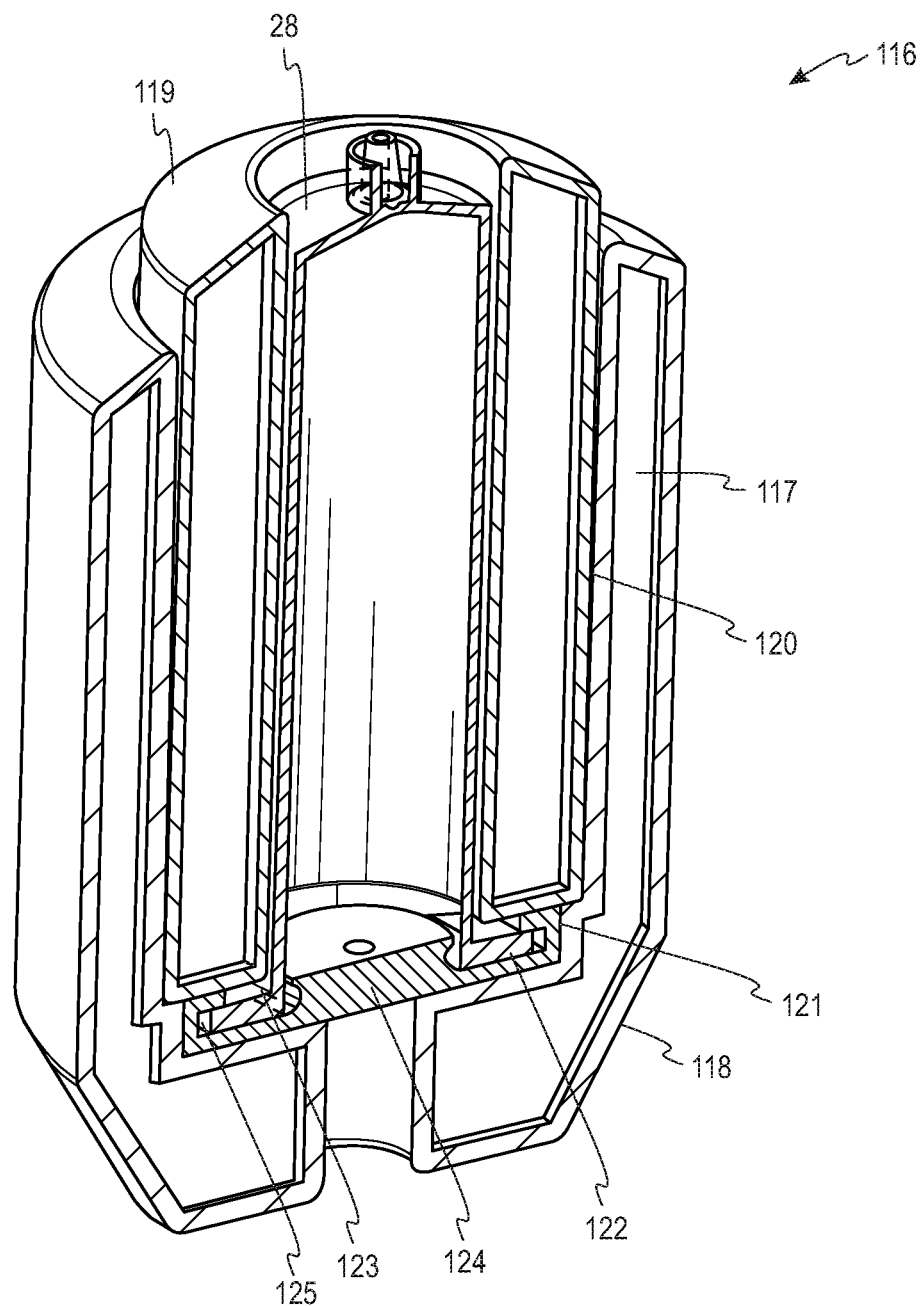
FIG. 7A is a longitudinal cross-section view of a syringe holder suitable for use with a syringe during centrifugation, according to an exemplary embodiment.

FIG. 7A shows a longitudinal cross-section of a syringe holder 116 that may be used to hold the syringe 28 during centrifugation, according to an exemplary embodiment. The syringe holder 116 may be configured for centrifugation in a commercially available blood banking centrifuge, such as a Sorvall Blood Processing Centrifuge capable of centrifuging, e.g., 2000-mL bottles, although the syringe holder may be configured for any number of centrifuge sizes and types. The holder 116 may comprise an outermost shell 117 comprising an outer contour 118 conforming to a rotor cavity of the desired centrifuge size/type. The holder 116 may comprise an inner shell 119 configured to fit concentrically within the inner contour 120 of the outermost shell 117. The inner contour 120 of the outermost shell 117 may comprise a tapered end 121 forming a recess 121 below the inner shell 119 when the inner shell is fully inserted into the outer shell 117. The recess 121 may be configured for receiving flanges 122 of the syringe 28 that may be secured in place within the recess 121 by the bottom surface 123 of the inner shell 119. A top view of one embodiment of the outer shell 117 and recess 121 is shown in FIG. 7C. Alternatively, the recess 121 may be configured for receiving an indented cap 124 comprising indentations 125 within which the flanges 122 (FIG. 7A) of the syringe 28 may fit.

Figure 7B:
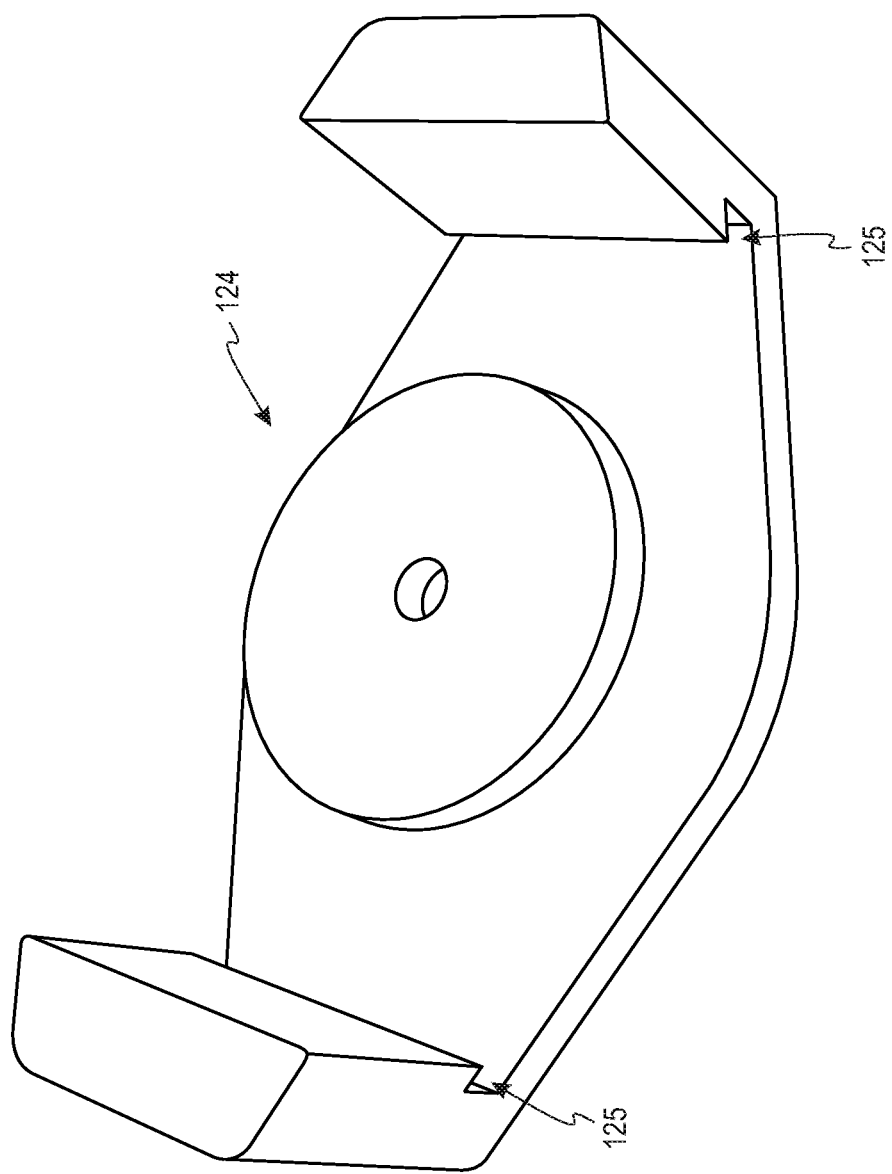
FIG. 7B is a perspective view of an indented cap suitable for use with the syringe holder of FIG. 7A, according to an exemplary embodiment.
Figure 7C:
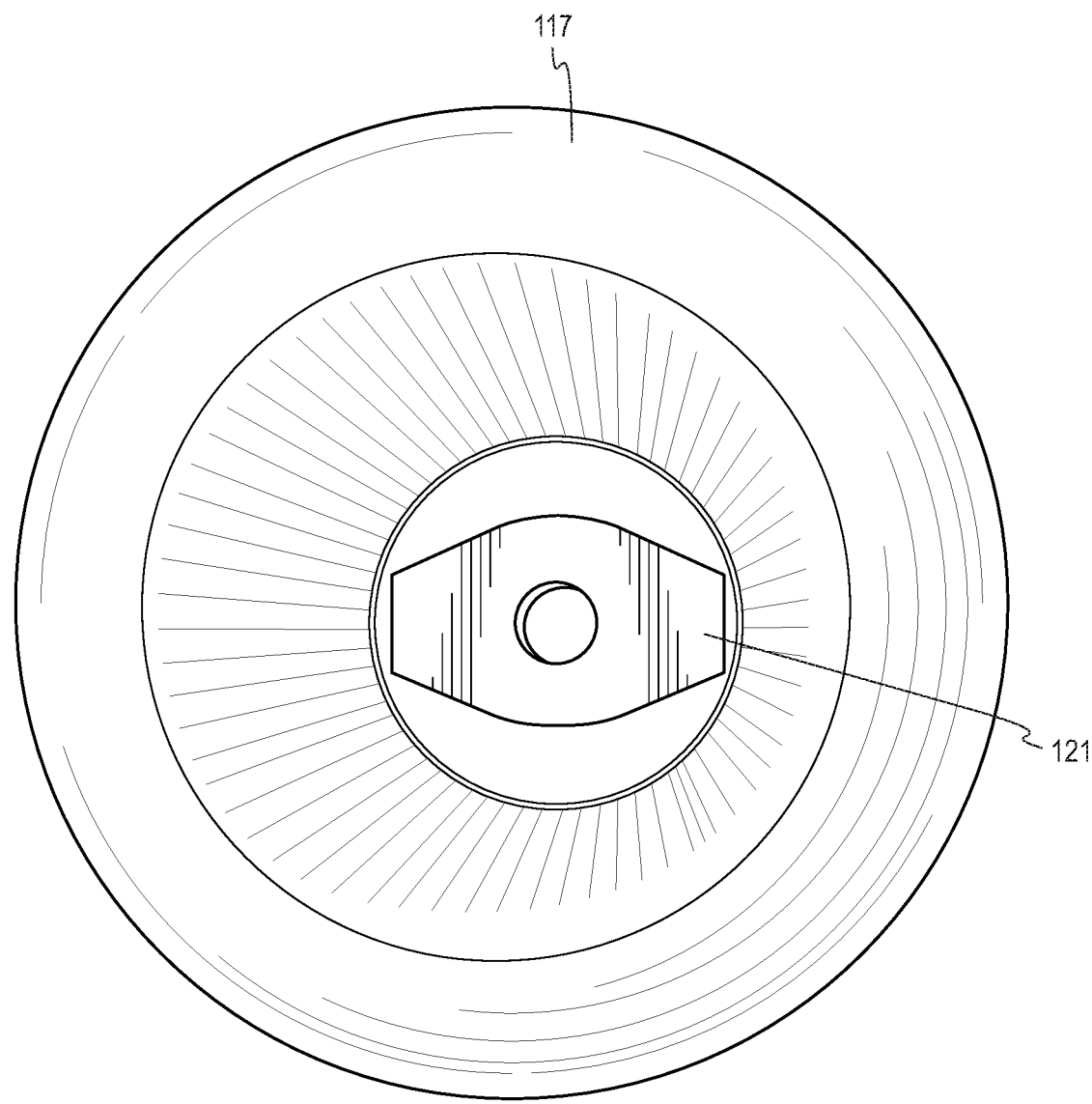
FIG. 7C is a top view of an outer shell of the syringe holder of FIG. 7A, according to an exemplary embodiment.

FIG. 7B is a perspective view of one embodiment of the indented cap 124, which may be removable from the outer shell 117 to fit the flanges 122 of the syringe. The indented cap 124, if used, may be provided as part of the syringe holder 116 or may be provided as a cap (e.g., cap 104 of FIG. 3) of the syringe 28.

In preparation for centrifugation, the flanges 122 of the syringe 28 containing the cell suspension may be placed into the recess 121 of the outer shell 117 (FIG. 7A) with the non-permeable tip 115 (FIG. 6) facing in the axial direction of centrifugation. If the indented cap 124 is to be used, with the indented cap 124 removed from the syringe holder 116, the flanges 122 may first be fitted within the indentations 125 of the indented cap 124 and then both the cap 124 and the flanges 122 together be placed into the recess 121 of the outer shell 117. The inner shell 119 may then be placed around the syringe 28 inside the outer shell 117, as shown in FIG. 7A. The syringe holder 116 containing the syringe 28 and cell suspension may then be ready for centrifugation.

The syringe holder 116 may be placed into a centrifuge rotor cavity (not illustrated) for which the syringe holder 116 was configured. In one embodiment, the cell suspension may be centrifuged at 1500 rpm for approximately 5 minutes, although any suitable centrifugation protocol may be implemented. Upon completion of centrifugation, the holder 116 containing the syringe 28 may be removed from the centrifuge, preferably while maintaining the non-permeable tip 115 oriented upwards. The inner shell 119 may be removed vertically from the outer shell 117, and the syringe 28 may likewise be removed vertically, care being taken to prevent remixing of pelletized cells.

Figure 8:
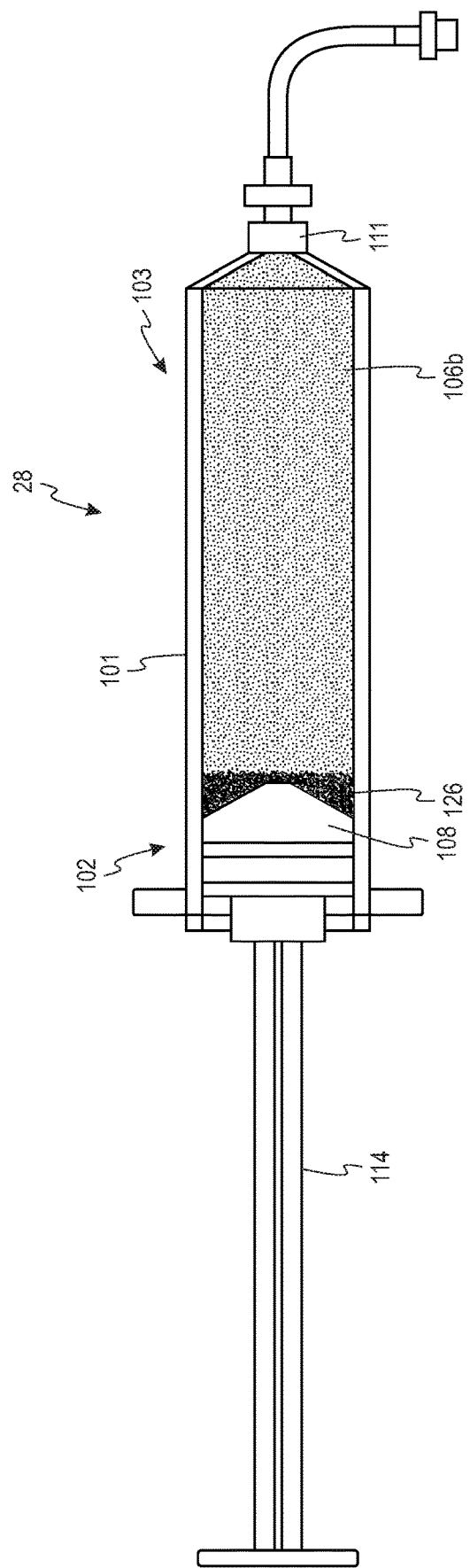
FIG. 8 is a diagrammatic view of a syringe containing pelletized cells ready for supernatant expression, according to an exemplary embodiment.

FIG. 8 shows the syringe 28 containing pelletized cells ready for supernatant expression. The indented cap 124 (FIG. 7B), if used, may first be removed from the flanges 122 of the syringe 28. The secondary cap 110 (FIG. 3), if used, may also be removed from the radial end 102 of the barrel 101. The non-permeable tip 115 that was put in place for centrifugation may be removed from the port 111 of the syringe 28 and replaced with a connection to any of the components of the disposable kit 14 (FIG. 2) or another fluid container or system. In an embodiment in which supernatant expression is performed manually or by a solid contact force mechanism, the cap 104 comprising the filter 105 may be removed. The handle 114 (FIG. 5A) configured for removable attachment with the plunger 108 may be attached to the plunger 108 from the radial end 102. In an embodiment in which supernatant expression is to be performed by a pneumatic mechanism, an air pump, e.g., pump 36 or 38 of FIG. 1, may be connected to the air vent 107 of the cap 104 (FIG. 4B) in lieu of the handle 114, for pneumatic supernatant expression.

Figure 9:
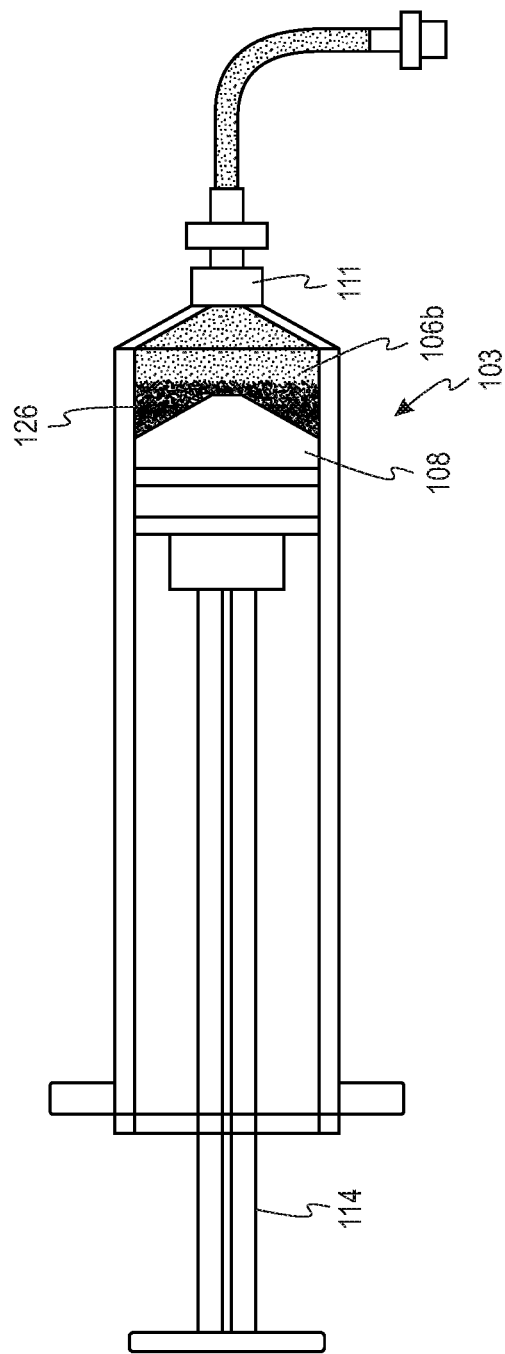
FIG. 9 is a diagrammatic view of a syringe containing a desired volume of supernatant, according to an exemplary embodiment.

To initiate supernatant expression, the plunger 108 may be pushed manually or via a machine towards the axial end 103, pushing the supernatant out of the axial side lumen 106b via the port 111. In one embodiment, the syringe 28 may be maintained at a tip-up orientation with the pelletized cells 126 disposed gravitationally below the port 111. FIG. 9 shows the plunger 108 pushed towards the axial end 103 until a desired volume of supernatant remains in the syringe 28. In an embodiment in which no supernatant is desired, the plunger 108 may be pushed towards the axial end 103 until all the supernatant save the pelletized cells 126 is expressed out of the port 111. Once the desired volume of supernatant has been expressed out, the plunger 108 may optionally be pulled slightly back towards the radial end 102 of the barrel 101 to draw air into the axial side lumen 106b to aid in later resuspension of the pelletized cells 126.

Figure 10:
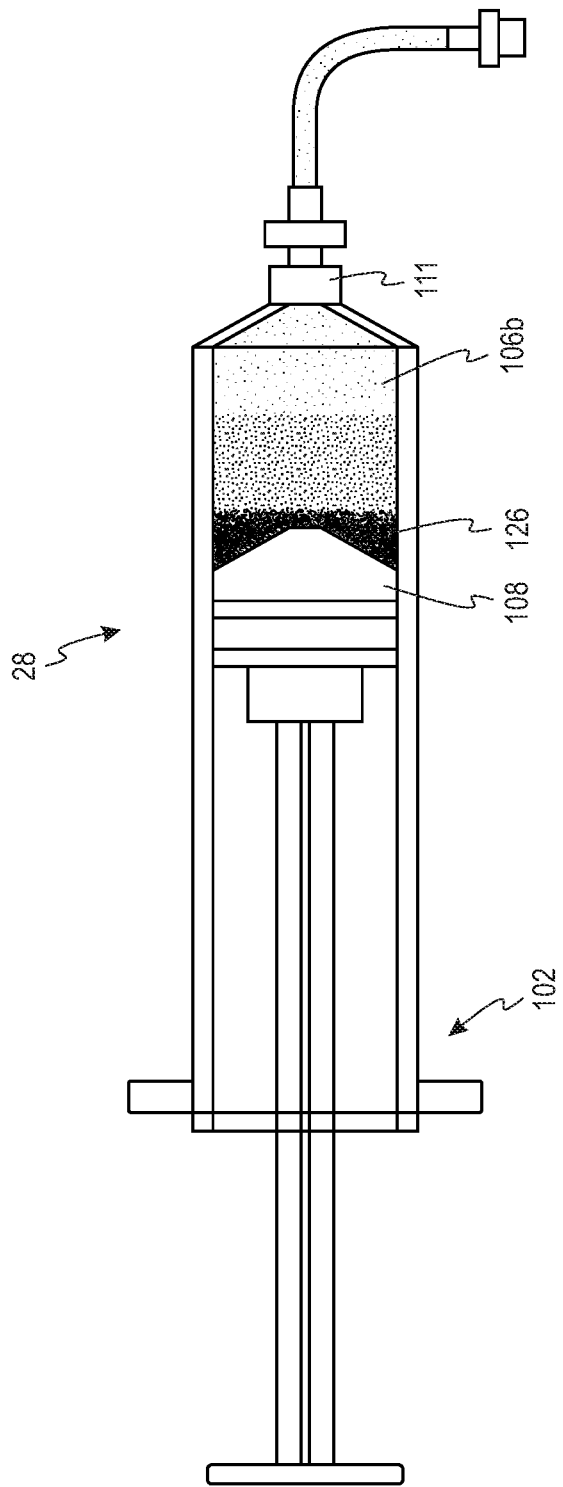
FIG. 10 is a diagrammatic view of a syringe having drawn additional resuspension media in preparation for resuspension, according to an exemplary embodiment.

In an embodiment in which no additional media is used for resuspending cells, resuspension of the pelletized cells 126 may be performed with the volume of supernatant remaining in the axial side lumen 106b. The syringe 28 may be gently agitated to resuspend the pelletized cells 126 in the remaining volume of supernatant. In an embodiment in which additional media is used for resuspending cells, the port 111 of the syringe 29 may be connected to a resuspension media source to draw in a desired volume of resuspension media into the axial side lumen 106b by actuating the plunger 108 towards the radial end 102, as shown in FIG. 10. Whether additional media is or is not used for resuspending cells, the volume of cell suspension in the axial side lumen 106b of the syringe 28 after resuspension now contains the final concentration and final volume desired for subsequent use of the cells. This cell product may then be expressed into a final container or vial by actuating the plunger 108 manually or by machine completely against the axial end 103, pushing the resuspended cells out of the axial side lumen 106b via the port 111. If desired, a small amount, e.g., less than 1 mL of the resuspended cells or wash media may be drawn back into the axial side lumen 106 to wash any remaining cells remaining in the syringe 28.

Without limiting the foregoing description, in accordance with one aspect of the subject matter herein, there is provided a system for concentrating cells. A syringe comprises a lumen and an axial end comprising a port and a radial end closed to liquid flow. A plunger divides the axial and radial ends, and the syringe is configured to hold a cellular suspension. A filter disposed at the radial end configured to maintain sterility of the syringe. A cap comprises a vent disposed at the radial end. The plunger is configured to be actuated towards the axial end by air pressure being applied into the radial end and the plunger is configured to be actuated towards the radial end by a vacuum being applied into the radial end.

In accordance with a second aspect which may be used or combined with the immediately preceding aspect, an actuator handle is configured for attachment with a radial side of the plunger for actuation using a solid contact force. The filter and the cap are removable from the radial end of the syringe.

In accordance with a third aspect which may be used or combined with any of the preceding aspects, the plunger comprises a visible indicator indicative of a relative position of the plunger between the axial and radial ends.

In accordance with a fourth aspect which may be used or combined with any of the preceding aspects, the lumen of the syringe comprises a capacity of 50-60 mL.

In accordance with a fifth aspect which may be used or combined with any of the preceding aspects, a syringe holder is configured to fit in a cavity of a centrifuge rotor having an axis of rotation. The syringe holder is configured to receive the syringe containing the cellular suspension with the axial end disposed towards an axial direction relative to the axis of rotation and the radial end disposed towards a radial direction relative to the axis of rotation.

In accordance with a sixth aspect which may be used or combined with the fifth aspect, the syringe holder comprises an inner shell configured to fit concentrically within an outer shell having an end forming a recess when the inner shell is fully inserted into the outer shell.

In accordance with a seventh aspect which may be used or combined with the sixth aspect, the recess of the outer shell is configured to receive the radial end of the syringe, and wherein the inner shell is configured to secure the syringe in place within the outer shell when the inner shell is fully inserted into the outer shell.

In accordance with an eighth aspect which may be used or combined with the seventh aspect, the radial end of the syringe comprises flanges configured to fit within the recess of the outer shell.

In accordance with a ninth aspect which may be used or combined with any of the preceding aspects, the filter comprises a filter having pore sizes in the range of 0.2 to 0.45 microns.

In accordance with a tenth aspect, there is provided a method concentrating a cell suspension with a centrifuge. Provided is a syringe comprising an axial end comprising a port and a radial end closed to liquid flow. A plunger divides the axial and radial ends, and the syringe is configured to hold a cellular suspension. Provided is a syringe holder configured to fit in a cavity of a centrifuge rotor having an axis of rotation. The syringe holder is configured to receive the syringe containing the cellular suspension with the axial end disposed towards an axial direction relative to the axis of rotation and the radial end disposed towards a radial direction relative to the axis of rotation. A first volume of the cell suspension is drawn into the axial end of the syringe. The syringe containing the first volume is centrifuged within the syringe holder with the port of the axial end disposed closer to the axis of rotation relative to the radial end of the syringe. Centrifuging is performed until the first volume is separated into pelletized cells and a supernatant. The supernatant is expressed off from the syringe until the axial end of the syringe comprises the pelletized cells and a desired volume of supernatant. The pelletized cells are resuspended in the desired volume of supernatant to arrive at a final cell product.

In accordance with an eleventh aspect which may be used or combined with any of the tenth aspect, the first volume of the cell suspension comprises a volume equal to or less than 50-60 mL.

In accordance with a twelfth aspect which may be used or combined with any of the tenth and eleventh aspects, provided is a pneumatic pump configured for connection with the radial end of the syringe. Drawing the first volume or expressing off the supernatant is performed by the pneumatic pump.

In accordance with a thirteenth aspect which may be used or combined with any of the tenth through twelfth aspects, provided is an actuator configured for attachment with a radial side of the plunger. The first volume is drawn by pulling the actuator towards the radial end. The supernatant is expressed off by pushing the actuator towards the axial end.

In accordance with a fourteenth aspect which may be used or combined with any of the tenth through thirteenth aspects, the syringe holder is configured to fit into a cavity of a centrifuge rotor configured to centrifuge a 2000-mL bottle.

In accordance with a fifteenth aspect which may be used or combined with any of the tenth through fourteenth aspects, the syringe holder is configured to receive a syringe comprising a capacity of 50-60 mL.

In accordance with a sixteenth aspect which may be used or combined with any of the tenth through fifteenth aspects, the syringe holder comprises an inner shell configured to fit concentrically within an outer shell having an end forming a recess when the inner shell is fully inserted into the outer shell.

In accordance with a seventeenth aspect which may be used or combined with the sixteenth aspect, the recess of the outer shell is configured to receive the radial end of the syringe, and wherein the inner shell is configured to secure the syringe in place within the outer shell when the inner shell is fully inserted into the outer shell.

In accordance with an eighteenth aspect which may be used or combined with any of the tenth through seventeenth aspects, expressing off the supernatant from the syringe is performed with the port of the syringe disposed gravitationally above the plunger.

In accordance with a nineteenth aspect which may be used or combined with any of the tenth through eighteenth aspects, after the step of expressing off the supernatant and prior to resuspending the pelletized cells, a small volume of new media is drawn into the syringe in preparation for resuspension to arrive at the final cell product.

In accordance with a twentieth aspect which may be used or combined with any of the tenth through nineteenth aspects, the first volume of cell suspension comprises at least one of red blood cells, white blood cells, and platelets.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A system for concentrating cells, comprising:
   a syringe comprising a lumen and an axial end comprising a port and a radial end closed to liquid flow, wherein a plunger divides the axial and radial ends, and wherein the syringe is configured to hold a cellular suspension;
   a filter disposed at the radial end configured to maintain sterility of the syringe;
   a cap comprising a vent disposed at the radial end; and
   a syringe holder comprising an inner shell configured to fit concentrically within an outer shell having an end forming a recess when the inner shell is fully inserted into the outer shell, wherein
      the syringe holder is configured to fit in a cavity of a centrifuge rotor having an axis of rotation and the syringe holder is configured to receive the syringe containing the cellular suspension with the axial end disposed towards an axial direction relative to the axis of rotation and the radial end disposed towards a radial direction relative to the axis of rotation, and
      the plunger is configured to be actuated towards the axial end by air pressure being applied into the radial end and the plunger is configured to be actuated towards the radial end by a vacuum being applied into the radial end.

2. The system of claim 1, further comprising an actuator handle configured for attachment with a radial side of the plunger for actuation using a solid contact force, and wherein the filter and the cap are removable from the radial end of the syringe.

3. The system of claim 1, wherein the plunger comprises a visible indicator indicative of a relative position of the plunger between the axial and radial ends.

4. The system of claim 1, wherein the lumen of the syringe comprises a capacity of 50-60 mL.

5. The system of claim 1, wherein the recess of the outer shell is configured to receive the radial end of the syringe, and wherein the inner shell is configured to secure the syringe in place within the outer shell when the inner shell is fully inserted into the outer shell.

6. The system of claim 5, wherein the radial end of the syringe comprises flanges configured to fit within the recess of the outer shell.

7. The system of claim 1, wherein the filter comprises a filter having pore sizes in the range of 0.2 to 0.45 microns.

8. A method of concentrating a cell suspension with a centrifuge, comprising:
   mounting a syringe within a syringe holder in a cavity of a centrifuge rotor having an axis of rotation, wherein
      the syringe holds a cellular suspension and comprises comprising an axial end comprising a port and a radial end closed to liquid flow, with a plunger dividing the axial and radial ends;
      the syringe holder comprises an inner shell configured to fit concentrically within an outer shell having an end forming a recess when the inner shell is fully inserted into the outer shell, with the syringe holder receiving the syringe with the axial end disposed towards an axial direction relative to the axis of rotation and the radial end disposed towards a radial direction relative to the axis of rotation;
   drawing a first volume of the cell suspension into the axial end of the syringe;
   centrifuging the syringe containing the first volume within the syringe holder with the port of the axial end disposed closer to the axis of rotation relative to the radial end of the syringe, wherein centrifuging is performed until the first volume is separated into pelletized cells and a supernatant;
   expressing off the supernatant from the syringe until the axial end of the syringe comprises the pelletized cells and a desired volume of supernatant; and
   resuspending the pelletized cells in the desired volume of supernatant to arrive at a final cell product, wherein the plunger is actuated towards the axial end by air pressure being applied into the radial end and actuated towards the radial end by a vacuum being applied into the radial end.

9. The method of claim 8, wherein the first volume of the cell suspension comprises a volume equal to or less than 50-60 mL.

10. The method of claim 8, further comprising providing a pneumatic pump configured for connection with the radial end of the syringe, wherein drawing the first volume or expressing off the supernatant is performed by the pneumatic pump.

11. The method of claim 8, further comprising:
   providing an actuator configured for attachment with a radial side of the plunger;
   drawing the first volume by pulling the actuator towards the radial end; and
   expressing off the supernatant by pushing the actuator towards the axial end.

12. The method of claim 8, wherein the syringe holder is configured to fit into a cavity of a centrifuge rotor configured to centrifuge a 2000-mL bottle.

13. The method of claim 8, wherein the syringe holder is configured to receive a syringe comprising a capacity of 50-60 mL.

14. The method of claim 8, wherein the recess of the outer shell is configured to receive the radial end of the syringe, and wherein the inner shell is configured to secure the syringe in place within the outer shell when the inner shell is fully inserted into the outer shell.

15. The method of claim 8, wherein expressing off the supernatant from the syringe is performed with the port of the syringe disposed gravitationally above the plunger.

16. The method of claim 8, wherein after the step of expressing off the supernatant and prior to resuspending the pelletized cells, a small volume of new media is drawn into the syringe in preparation for resuspension to arrive at the final cell product.

17. The method of claim 8, wherein the first volume of cell suspension comprises at least one of red blood cells, white blood cells, and platelets.

\* \* \* \* \*